(12) United States Patent
Iida et al.

(10) Patent No.: US 9,591,991 B2
(45) Date of Patent: Mar. 14, 2017

(54) POSITION DETECTION SYSTEM

(71) Applicant: OLYMPUS CORPORATION, Tokyo (JP)

(72) Inventors: Takahiro Iida, Hachioji (JP); Atsushi Kimura, Akiruno (JP); Atsushi Chiba, Hachioji (JP); Ryoji Sato, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/008,926

(22) Filed: Jan. 28, 2016

(65) Prior Publication Data

US 2016/0143559 A1 May 26, 2016

Related U.S. Application Data (63) Continuation of application No. PCT/JP2014/081781, filed on Dec. 1, 2014.

(30) Foreign Application Priority Data

Dec. 10, 2013 (JP) ................................ 2013-255445

(51) Int. Cl.
*A61B 5/00* (2006.01)
*A61B 5/06* (2006.01)
*A61B 1/04* (2006.01)

(52) U.S. Cl.
CPC .............. *A61B 5/062* (2013.01); *A61B 1/041* (2013.01)

(58) Field of Classification Search
CPC ................................ A61B 1/041; A61B 5/062
See application file for complete search history.

(56) References Cited

U.S. PATENT DOCUMENTS 8,298,136 B2  10/2012 Kimura et al.
9,002,434 B2   4/2015 Uchiyama et al.

FOREIGN PATENT DOCUMENTS

| JP | 2008-275395 A | 11/2008 |
| WO | WO 2007/064013 A1 | 6/2007 |
| WO | WO 2010/122823 A1 | 10/2010 |

OTHER PUBLICATIONS

International Search Report dated Mar. 10, 2015 issued in PCT/JP2014/081781.

*Primary Examiner* — Rajeev Siripurapu
(74) *Attorney, Agent, or Firm* — Scully, Scott, Murphy & Presser, PC (57) ABSTRACT

A position detection system for detecting a position of a capsule medical device is provided. The capsule medical device has a coil constituting a part of a resonance circuit to generate an AC magnetic field. The position detection system includes: sensing coils that detect the AC magnetic field and output detection signals; and a calculation unit that calculates the position of the capsule medical device based on the detection signals. The calculation unit: determines a sensing coil having a maximum amplitude of the AC magnetic field as a reference coil among the sensing coils based on amplitude values of the AC magnetic field detected by the sensing coils, the amplitude values being calculated based on the detection signals; and determines a polarity of each sensing coil based on a first detection signal from the reference coil and a second detection signal from each sensing coil other than the reference coil.

9 Claims, 11 Drawing Sheets

POSITION DETECTION SYSTEM

CROSS-REFERENCE TO RELATED APPLICATIONS

This application is a continuation of PCT international application Ser. No. PCT/JP2014/081781 filed on Dec. 1, 2014 which designates the United States, incorporated herein by reference, and which claims the benefit of priority from Japanese Patent Application No. 2013-255445, filed on Dec. 10, 2013, incorporated herein by reference.

BACKGROUND

1. Technical Field

The disclosure relates to a position detection system for detecting a position of a capsule medical device introduced into a subject.

2. Related Art

In the related art, there has been developed a capsule medical device which is introduced into a subject to acquire various types of information on internal portions of the subject or to administer drugs into the subject. As an example, in the field of endoscope, there is known a capsule endoscope having a size enough to be introduced into the gastrointestinal tract (lumen) of a subject. The capsule endoscope has an imaging function and a wireless communication function inside a capsule-shaped casing, and after being swallowed into the subject, the capsule endoscope performs imaging while moving along the gastrointestinal tract by peristaltic movement or the like and sequentially transmits images (hereinafter, referred to as in-vivo images) of organs of the subject wirelessly. The wirelessly transmitted image data is received by a receiving device provided outside the subject and is further received into an image processing device such as a workstation, where a predetermined image process is performed. Therefore, in the image processing device, an in-vivo image of the subject is reproduced and displayed as a still image or a moving image.

In order to identify a portion of the subject in such an in-vivo image, a position detection system for detecting a position or posture of a capsule medical device in the subject has been developed (See International Publication Pamphlet No. WO 2007/064013 and Japanese Patent Application Laid-open No. 2008-275395). For example, WO 2007/064013 discloses a technique where a coil (marker coil) for generating an alternate-current (AC) magnetic field is provided in a capsule medical device, the AC magnetic field generated by the marker coil is detected by a plurality of coils (hereinafter, referred to as sensing coils) provided outside a subject for detection of the magnetic field, and a position of the capsule medical device is estimated based on a strength of the detected AC magnetic field.

However, in order to improve the accuracy of detection of the capsule medical device in the position detection system, incident direction of the AC magnetic field incident on the sensing coil, that is, the polarity of the sensing coil needs to be determined. In the related art, the magnetic field is detected by the sensing coil in synchronization with the generation of the magnetic field from the marker coil, and the polarity determination is performed based on the phase difference between the generated magnetic field and the detected magnetic field. For example, if the generated magnetic field and the detected magnetic field are in phase, the polarity is determined to be plus; and if the generated magnetic field is out of phase with the detected magnetic field by n) (180°, the polarity is determined to be minus.

SUMMARY

In some embodiments, a position detection system for detecting a position of a capsule medical device is provided. The capsule medical device has: a coil constituting a part of a resonance circuit to generate an AC magnetic field by flowing of current; a power source unit for supplying power to the coil; and a capsule casing, the coil and the power source unit being provided inside the casing. The position detection system includes: a plurality of sensing coils configured to detect the AC magnetic field generated by the coil and to output detection signals; and a calculation unit configured to calculate the position of the capsule medical device based on the plurality of detection signals output from the plurality of sensing coils. The calculation unit includes: a reference coil determination unit configured to determine a sensing coil having a maximum amplitude value of the AC magnetic field as a reference coil among the plurality of sensing coils based on amplitude values of the AC magnetic field detected by the plurality of sensing coils, the amplitude values being calculated based on the plurality of detection signals; and a polarity determination unit configured to determine a polarity of each of the sensing coils based on a first detection signal output from the reference coil and a second detection signal output from each of the sensing coils other than the reference coil.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, a position detection system according to some embodiments of the present invention will be described with reference to the drawings. As a capsule medical device which is a detection target of the position detection system according to some embodiments, a capsule endoscope which is introduced into a subject through mouth to image an inside of the subject (lumen) will be exemplified. However, the present invention is not limited by the embodiments. That is, the present invention can be applied to position detection for various medical devices, such as a capsule endoscope which moves in the lumen from the esophagus to the anus of a subject, a capsule medical device which delivers drugs or the like to an inside of a subject, a capsule medical device provided with a pH sensor for measuring pH in a subject, and the like.

In the description hereinafter, shapes, sizes, and position relations in figures are schematically illustrated to such an extent that the content of the present invention can be understood. Therefore, the present invention is not limited to only the shapes, size, and position relations exemplified in the figures. The same reference signs are used to designate the same elements throughout the drawings.

First Embodiment

Figure 1:
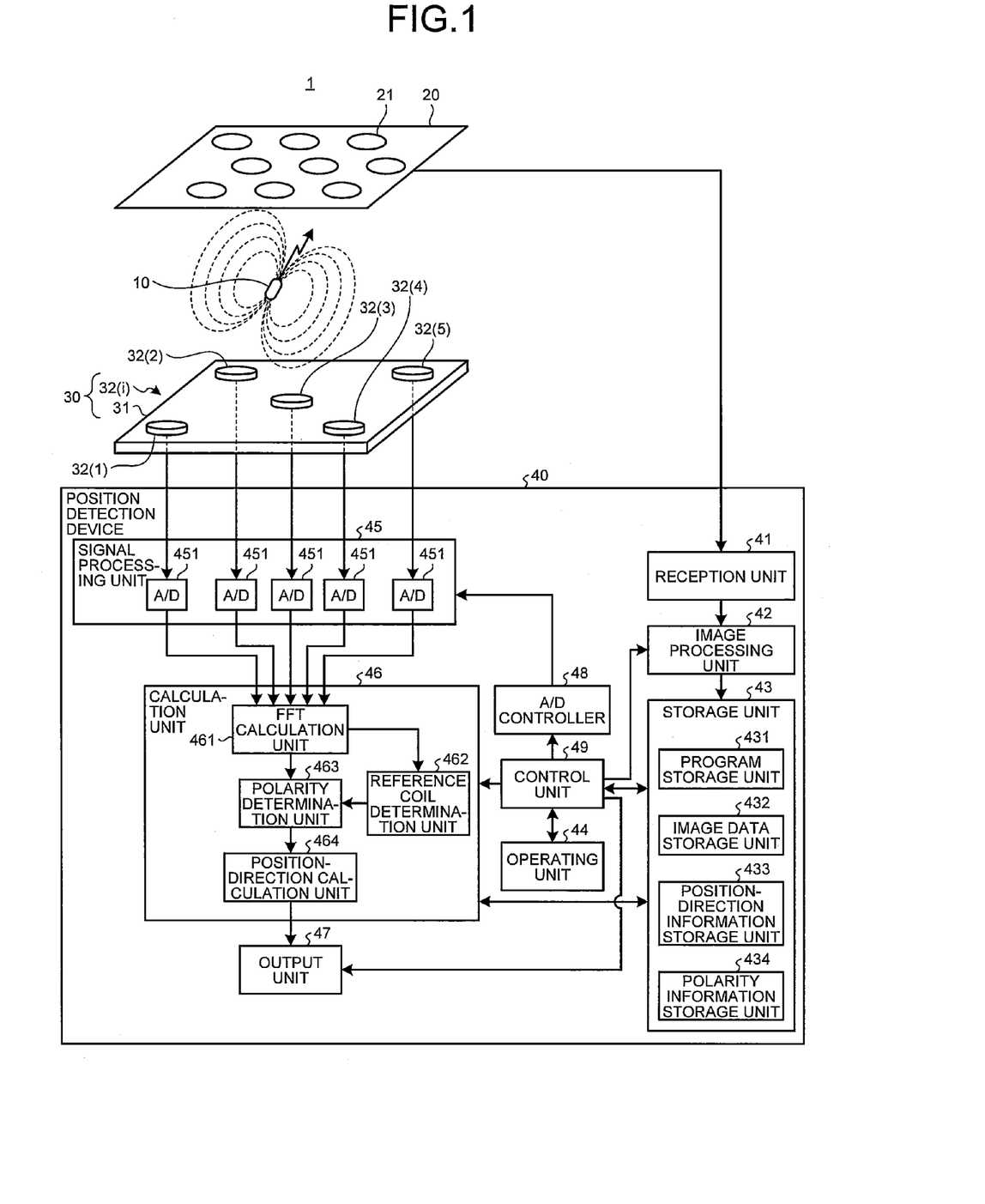
FIG. 1 is a schematic diagram illustrating a configuration example of a position detection system according to a first embodiment of the present invention.

FIG. 1 is a schematic diagram illustrating a configuration example of a position detection system according to a first embodiment of the present invention. As illustrated in FIG. 1, the position detection system 1 according to the first embodiment includes: a capsule endoscope 10 which images an inside of the subject to acquire image data and transmit the image data so as to be superimposed on a radio signal, as an example of a capsule medical device which is introduced into a lumen of the subject; an antenna unit 20 which receives the radio signal transmitted from the capsule endoscope 10; a magnetic field detector 30 which detect an AC magnetic field generated from the capsule endoscope 10; and a position detection device 40 which generates an image of the inside of the subject based on the radio signal transmitted from the capsule endoscope 10 and detects a position of the capsule endoscope 10 based on the AC magnetic field detected by the magnetic field detector 30.

Figure 2:
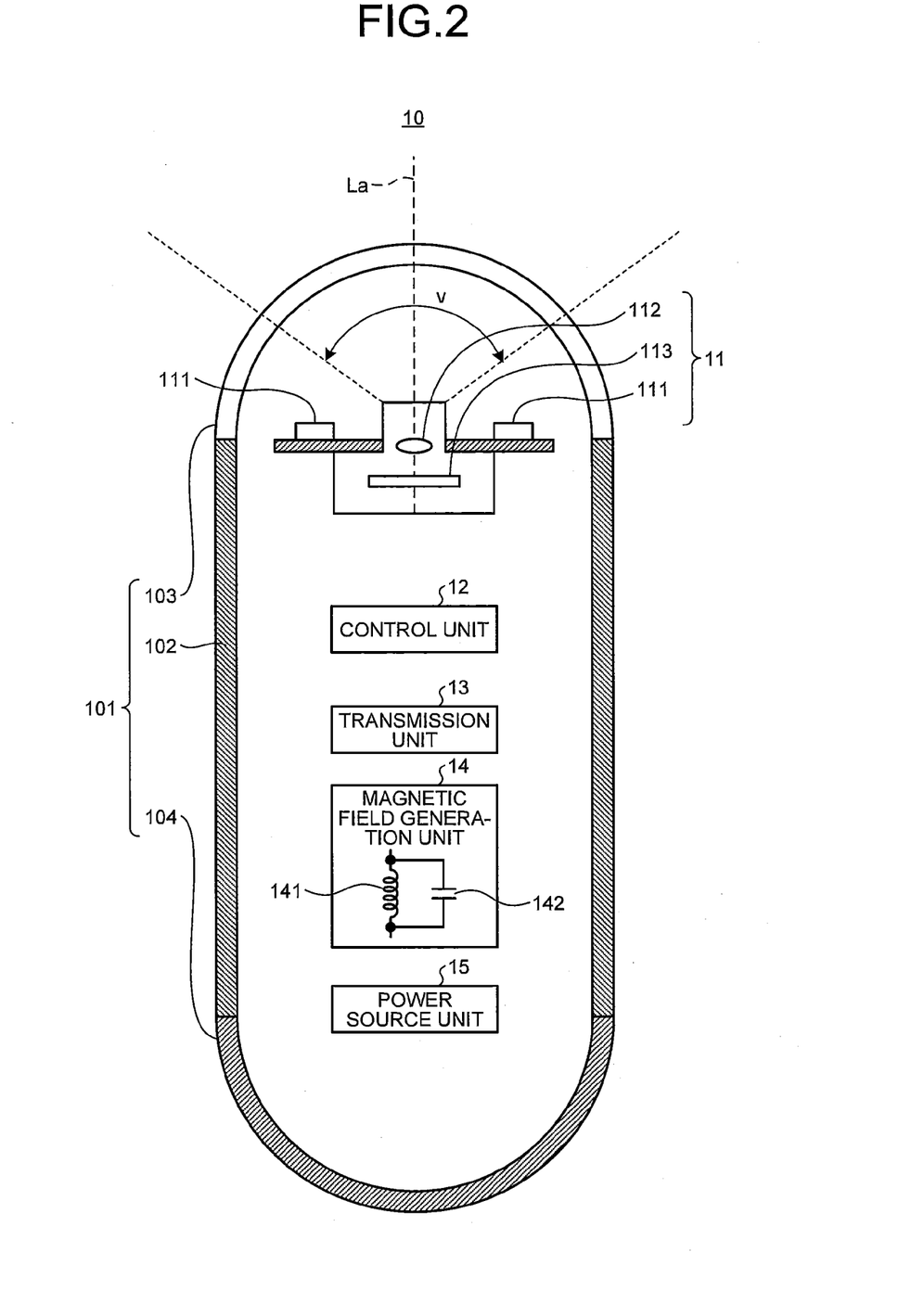
FIG. 2 is a schematic diagram illustrating an example of an internal structure of a capsule endoscope illustrated in FIG. 1.

FIG. 2 is a schematic diagram illustrating an example of an internal structure of the capsule endoscope 10 illustrated in FIG. 1. As illustrated in FIG. 2, the capsule endoscope 10 includes a capsule-shaped casing 101 having a size enough to be easily introduced into the lumen of the subject, an imaging unit 11 which is housed in the casing 101 to image the inside of the subject to acquire an imaging signal, a control unit 12 which controls operations of components of the capsule endoscope 10 including the imaging unit 11 and performs a predetermined signal process on the imaging signal acquired by the imaging unit 11, a transmission unit 13 which wirelessly transmits the imaging signal subject to the signal process, a magnetic field generation unit 14 which generates an AC magnetic field for detecting a position of the capsule endoscope 10, and a power source unit 15 which supplies power to the components of the capsule endoscope 10.

The casing 101 is an outer casing having a size enough to be introduced into an organ of the subject. The casing 101 includes a cylindrical casing 102 having a cylindrical shape and dome-shaped casings 103 and 104 each having a dome shape, and both open ends of the cylindrical casing 102 are closed by the dome-shaped casings 103 and 104. The cylindrical casing 102 is formed of a colored member which is substantially opaque to visible light. At least one of the dome-shaped casings 103 and 104 (in FIG. 2, the dome-shaped casing 103 close to the imaging unit 11) is formed of an optical member which is transparent to light of a predetermined wavelength band such as visible light. In FIG. 2, one imaging unit 11 is provided only in the dome-shaped casing 103 side. However, two imaging units 11 may be provided, and in this case, the dome-shaped casing 104 is also formed of a transparent optical member. The casing 101 houses the imaging unit 11, the control unit 12, the transmission unit 13, the magnetic field generation unit 14, and the power source unit 15 in a liquid-tightened manner.

The imaging unit 11 is an information acquisition unit which acquires an imaging signal as information on the subject, and includes an illumination unit 111 including a light-emitting element such as an LED and a driving circuit (not illustrated) driving the light-emitting element, an optical system 112 of a condensing lens and the like, and an imaging member 113 including an imaging element such as a CMOS image sensor or a CCD and a driving circuit (not illustrated) which drives the imaging element. The illumination unit 111 irradiates an imaging field of view of the imaging member 113 with white light or the like to illuminate the subject in the imaging field of view v through the dome-shaped casing 103. The optical system 112 is arranged such that the optical axis La is coincident with the longitudinal axis of the casing 101, and the optical system condenses reflected light from the subject within the imaging field of view v to form an image on the imaging plane of the imaging member 113. The imaging member 113 performs a photoelectric conversion process on an optical signal indicating the image of the subject formed on the imaging plane to generate an imaging signal.

If two imaging units 11 are employed, the two imaging units 11 are arranged at the dome-shaped casings 103 side and the dome-shaped casings 104 side at both ends of the casing 101 such that both optical axes La of the two optical systems 112 are coincident with the longitudinal axis of the casing 101.

The control unit 12 controls the imaging member 113 to be operated in a predetermined period (imaging frame rate) and controls the illumination unit 111 to emit light in synchronization with the imaging frame rate. Further, the control unit 12 performs A/D conversion or other predetermined signal processes on the imaging signal generated by the imaging unit 11 to generate image data. In addition, the control unit 12 controls the power source unit 15 to supply power to the magnetic field generation unit 14, so that the magnetic field generation unit 14 generates the AC magnetic field.

The transmission unit 13 includes a transmission antenna (not illustrated) and acquires the image data subject to the signal processes by the control unit 12 and associated information, performs modulation on the data and information, and sequentially transmits the modulated data and information through the transmission antenna to the outside.

The magnetic field generation unit 14 includes a coil or a resonance circuit having a coil and a capacitor. For example, the magnetic field generation unit 14 includes a marker coil 141 for generating a magnetic field by flowing of current and a capacitor 142. The marker coil 141 and the capacitor 142 constitute the resonance circuit. The magnetic field generation unit 14 is supplied with power from the power source unit 15 to generate the AC magnetic field having a predetermined frequency.

The power source unit 15 includes, for example, a button-type battery and a switch member such as a magnetic switch. The power source unit 15 switches the magnetic switch according to the magnetic field applied from the outside to switch its own On/Off state and supplies power to the components of the capsule endoscope 10 during the On state. In addition, the power source unit 15 stops supplying power to the components of the capsule endoscope 10 during the Off state.

Referring to FIG. 1 again, the antenna unit 20 includes a plurality of receiving antennas 21 for receiving the radio signal transmitted from the capsule endoscope 10. The receiving antennas 21 are attached to a body surface of the subject when the examination by the capsule endoscope 10 is performed.

The magnetic field detector 30 includes a planar base 31 and a plurality (in FIG. 1, five) of sensing coils $32(i)$ arranged on a main plane of the base 31. Here, the symbol "i" denotes identification numbers of the sensing coils $32(i)$, and in the case of FIG. 1, i=1 to 5. Each of the sensing coils $32(i)$ is, for example, a cylindrical coil having an opening diameter of about 30 to 40 mm and a height of about 5 mm, and the sensing coil receives the AC magnetic field generated from the capsule endoscope 10 and converts to a voltage signal to output the voltage signal as a detection signal.

The magnetic field detector 30 is arranged in the vicinity of the subject during the examination by the capsule endoscope 10. For example, if the examination is performed while the subject lies on a bed or the like, the magnetic field detector 30 is arranged under the bed so that the main surface of the base 31 is parallel to a subject mounting plane.

As illustrated in FIG. 1, the position detection device 40 includes a reception unit 41 which receives the radio signal transmitted from the capsule endoscope 10 through the antenna unit 20, an image processing unit 42 which generates an image of the inside of the subject based on the image data superimposed on the radio signal, a storage unit 43 which stores various types of information such as the image data representing the image of the subject, an operating unit 44 which is used to input a command or information to the position detection device 40, a signal processing unit 45 which performs a signal process on the signal representing the AC magnetic field detected by the magnetic field detector 30, a calculation unit 46 which calculates the position and direction of the capsule endoscope 10 based on the AC magnetic field detected by the magnetic field detector 30, an output unit 47 which outputs various types of information such as the calculation result of the calculation unit 46, an A/D controller 48 which controls the signal processing unit 45, and a control unit 49 which controls operations of the components.

The reception unit 41 receives the radio signal from the antenna unit 20 and selects the antenna appropriate to the radio signal, for example, the receiving antenna 21 having the highest reception strength among the receiving antennas 21 and performs a demodulation process or the like on the radio signal received through the selected receiving antenna 21 to acquire image data and associated information.

In the first embodiment, for simplifying the configuration, the function of receiving the radio signal transmitted from the capsule endoscope 10 is included in the position detection device 40, but the function of receiving the radio signal is not necessarily included in the position detection device 40.

The image processing unit 42 performs predetermined image processes such as white balance processing, demosaicing, gamma conversion, smoothing (noise elimination or the like), and the like on the image data input from the reception unit 41 to generate image data for display.

The storage unit 43 is configured by using a storage medium which stores information in a rewritable manner such as flash memory or a hard disk drive and a read/write device. The storage unit 43 includes a program storage unit 431 which stores various types of programs and various types of parameters for the control unit 49 controlling the components of the position detection device 40, an image data storage unit 432 which stores the image data generated by the image processing unit 42 and associated information, a position-direction information storage unit 433 which stores the calculation result of the position and direction of the capsule endoscope 10, and a polarity information storage unit 434 which stores polarities (incident directions of the AC magnetic field incident on the sensing coils $32(i)$) of the sensing coils $32(i)$ when the position and direction of the capsule endoscope 10 are calculated.

The operating unit 44 includes an input device such as various buttons, switches, or a keyboard, a pointing device such as a mouse or a touch panel, or a joystick and inputs various types of information to the control unit 49 in response to user's input manipulation. As the information input by the operating unit 44, for example, there is information (hereinafter, referred to as guiding instruction information) for guiding the capsule endoscope 10 to a position and posture which are desired by the user.

The signal processing unit 45 includes a plurality of A/D converters (A/D) 451 which receives respective voltage signals output from the plurality of sensing coils $32(i)$. Each A/D converter 451 performs an A/D conversion process on the analog voltage signal received from the corresponding sensing coil $32(i)$ and outputs the converted voltage as the detection data of the magnetic field.

The calculation unit 46 is configured by using, for example, hardware of a CPU and the like and reads a calculation program from the storage unit 43 and calculates information (position information) indicating the position of the capsule endoscope 10 based on the detection data of the magnetic field output from the signal processing unit 45. More specifically, the calculation unit 46 includes an FFT calculation unit 461, a reference coil determination unit 462, a polarity determination unit 463, and a position-direction calculation unit 464.

The FFT calculation unit 461 performs a fast Fourier transform (hereinafter, referred to as FFT) process on the detection data output from the A/D converter 451 based on a clock phase of the position detection device 40 side to extract magnetic field information such as an amplitude or a phase of the AC magnetic field.

The reference coil determination unit 462 determines the sensing coil $32(i)$ having the maximum amplitude value of the detected magnetic field among the plurality of sensing coils $32(i)$ as a reference coil.

The polarity determination unit 463 determines the polarities of the sensing coils $32(i)$ (incidence direction of the AC magnetic field) based on the FFT calculation results for the detection data output from the A/D converters 451 and the FFT calculation result for the detection data output from the A/D converter 451 corresponding to the reference coil and stores the determination result in the storage unit 43.

The position-direction calculation unit 464 calculates the position and direction of the marker coil 141, that is, the position and direction of the capsule endoscope 10 based on the amplitude values of the magnetic field detected by the sensing coils 32(i), the polarities of the sensing coils 32(i), and the positions and directions of the sensing coils 32(i).

The output unit 47 includes various types of display such as a liquid crystal display or an organic EL display and displays the calculation results for the position and direction of the capsule endoscope 10 by the position-direction calculation unit 464, the image of the inside of the subject generated by the image processing unit 42, various types of information input from the operating unit 44, and the like on a screen.

The A/D controller 48 outputs a control signal (A/D conversion trigger) for operating the plurality of A/D converters 451 in synchronization with one another in a predetermined period. Therefore, at the same timing, the plurality of A/D converters 451 receive the detection signals from the respective sensing coils 32(i) in the predetermined period and performs the A/D conversion process.

The control unit 49 is configured by using, for example, hardware such as a CPU. The control unit 49 reads a program from the storage unit 43, sends out commands and executes data transmission to each component of the position detection device 40 to overall control the operations of the position detection device 40.

Figure 3:
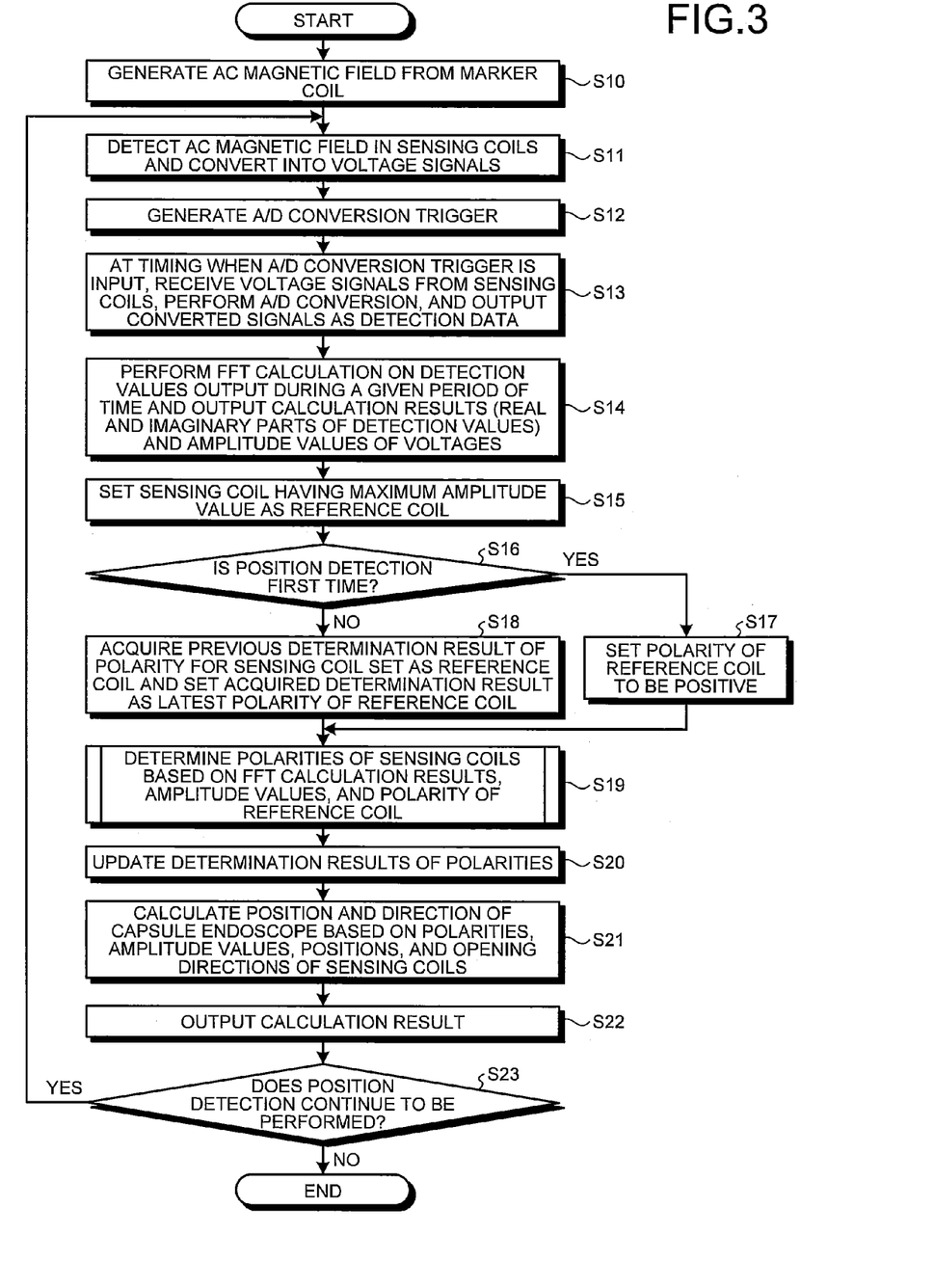
FIG. 3 is a flowchart illustrating operations of the position detection system illustrated in FIG. 1.

Next, the operations of the position detection system 1 will be described. FIG. 3 is a flowchart illustrating the operations of the position detection system 1. When performing the examination by the capsule endoscope 10, first, the capsule endoscope 10 is powered on. Therefore, the imaging member 113 starts an imaging operation, and the magnetic field generation unit 14 is driven, so that AC magnetic field having a predetermined driving frequency is generated from the marker coil 141 (step S10). If the capsule endoscope 10 is introduced into the inside of the subject, the capsule endoscope 10 moves in the lumen by peristaltic movement to perform imaging and wirelessly transmit the image data.

Subsequently, in step S11, the sensing coils 32(i) detects the AC magnetic field generated from the marker coil 141 and converts the detection signal into a voltage signal.

In step S12, the A/D controller 48 generates an A/D conversion trigger for operating the plurality of A/D converters 451 in synchronization with one another.

In step S13, at the timing when the A/D conversion trigger is received, the A/D converters 451 receive the voltage signals from the connected sensing coils 32(i), perform A/D conversion on the voltage signals, and output the converted signals as the detection data of the magnetic field.

In step S14, the FFT calculation unit 461 performs FFT calculation on the detection values of the voltages output as the detection data of the magnetic field during a given period of time from the A/D converters 451 and outputs the calculation result (real parts and imaginary parts of the detection values) and the amplitude values (absolute values) of the voltages. If the detection values V(i) as the FFT calculation results are expressed by $V(i)=x_{meas(i)}+jy_{meas(i)}$, the amplitude values $V_{abs(i)}$ are given by the following equation (1). Herein, the symbol $x_{meas(i)}$ denotes the real part of the detection value V(i), the symbol $y_{meas(i)}$ denotes the imaginary part of the detection value V(i), and the symbol j denotes a unit of an imaginary number.

$$V_{abs(i)}=\sqrt{x_{meas(i)}^2+y_{meas(i)}^2} \qquad (1)$$

In step S15, the reference coil determination unit 462 sets the sensing coil having the maximum amplitude value $V_{abs(i)}$ among the plurality of sensing coils 32(i) as a reference coil based on the calculation result of the FFT calculation unit 461.

Figure 4:
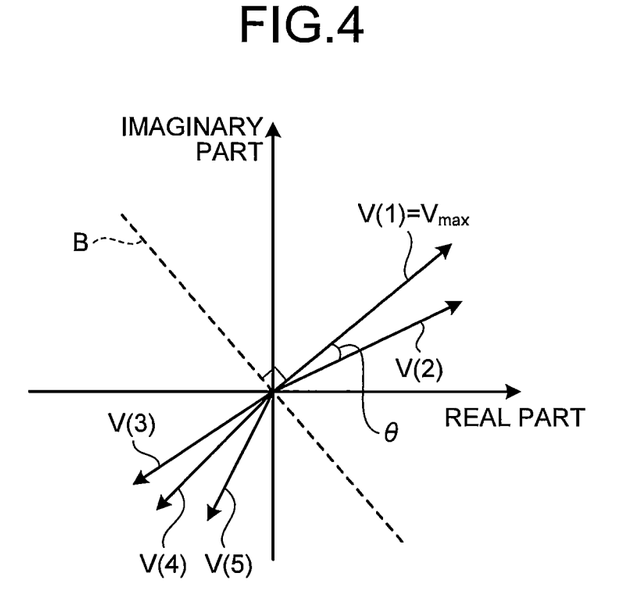
FIG. 4 is a schematic diagram illustrating detection values calculated through FFT calculation as vectors in an imaginary space.

FIG. 4 is a schematic diagram where the detection values V(i) (i=1 to 5) calculated through the FFT calculation are expressed by vectors in an imaginary space. In FIG. 4, as an example, the amplitude value $V_{abs(1)}$ of the detection value V(1) is set to the maximum value. In this case, the sensing coil 32(i) illustrated in FIG. 1 is set to the reference coil. Hereinafter, the detection value of the sensing coil 32(i) set as the reference coil is indicated by the detection value $V_{max}=x_{max}+jy_{max}$.

Subsequently, the polarity determination unit 463 sets the polarity of the reference coil. At this time, if the position detection for the capsule endoscope 10 is the first time in the current examination (step S16: Yes), polarity determination unit 463 sets the polarity of the reference coil to be positive (step S17). Even if the position detection for the capsule endoscope 10 is not the first time and if the previous determination result of polarity for the sensing coil 32(i) set as the reference coil cannot be obtained (i.e., the result is not stored in the polarity information storage unit 434), the polarity of the reference coil is set to be positive.

On the other hand, if the position detection for the capsule endoscope 10 is not the first time in the current examination (step S16: No), the polarity determination unit 463 acquires the previous determination result of polarity for the sensing coil 32(i) set as the reference coil from the storage unit 43 and sets the acquired determination result as the latest polarity of the reference coil (step S18). For example, in the case of FIG. 4, the previous determination result of polarity for the sensing coil 32(1) is set as the latest polarity of the reference coil.

In step S19, the polarity determination unit 463 determines the polarities of the sensing coils 32(i) based on the FFT calculation result (detection values V(i)), the amplitude values $V_{abs(i)}$ of the detection voltages and the polarity of the reference coil.

Figure 5:
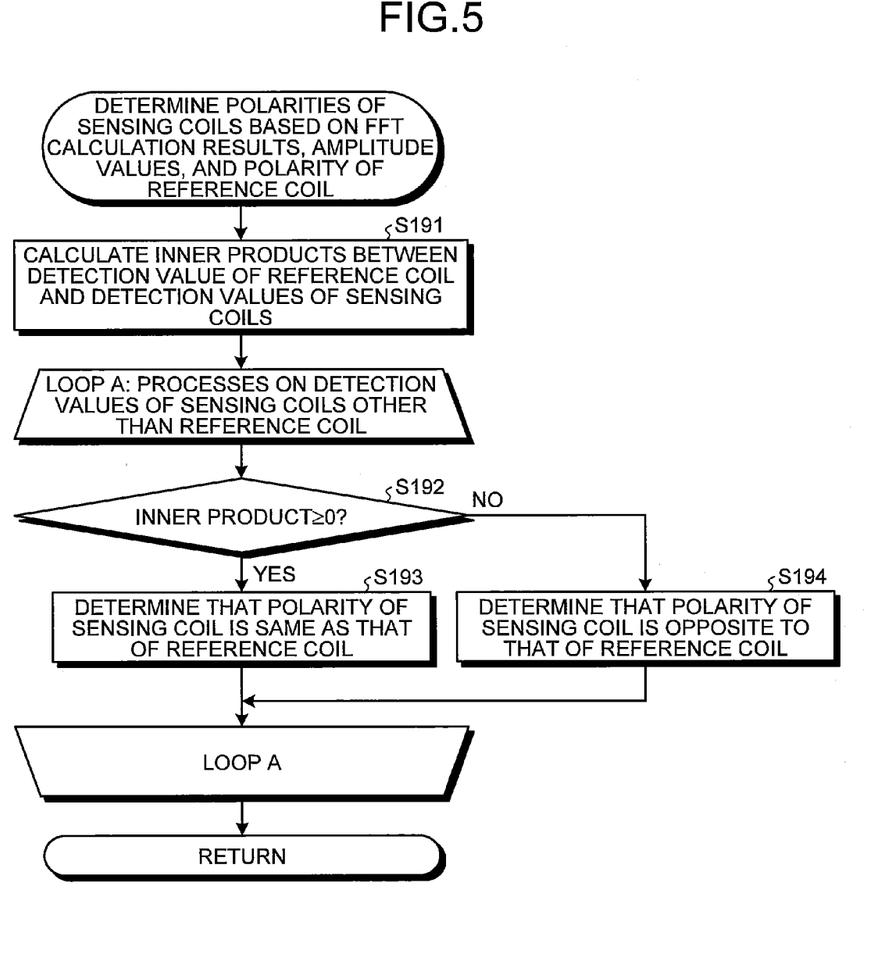
FIG. 5 is a flowchart illustrating a polarity determination process for sensing coils illustrated in FIG. 3.

FIG. 5 is a flowchart illustrating details of the process of determining the polarities of the sensing coils 32(i). First, in step S191, the polarity determination unit 463 calculates inner products $V_{max} \cdot V(i)$ between the detection value $V_{max}=x_{max}+jy_{meas(i)}$ of the reference coil and the detection values $V(i)=x_{meas(i)}+jy_{meas(i)}$ of the sensing coils 32(i). If the phase difference (in FIG. 4, angle between a reference vector indicating the detection value $V_{max}$ and the vector indicating the detection value V(2)) of the detection value V(i) with respect to the detection value $V_{max}$ is denoted by θ, the inner product $V_{max} \cdot V(i)$ is given by the following equation (2).

$$V_{max} \cdot V(i)=|V_{max}| \cdot |V(i)| \cdot \cos \theta \qquad (2)$$

Subsequently, the polarity determination unit 463 performs the process of a loop A on the detection values of the sensing coils 32(i) other than the reference coil.

In step S192, the polarity determination unit 463 determines whether or not the inner product $V_{max} \cdot V(i)$ calculated in step S191 is zero or positive.

If inner product $V_{max} \cdot V(i)$ is zero or positive (step S192: Yes), that is, if the phase difference θ between the phase of the detection value $V_{max}$ of the reference coil and the detection value V(i) of the sensing coil 32(i) is equal to or smaller than $|\pi/2|$, the polarity determination unit 463 determines that the polarity of the sensing coil 32(i) is equal to the polarity of the reference coil (step S193).

On the other hand, if the inner product $V_{max} \cdot V(i)$ is negative (step S192: No), that is, if the phase difference θ between the phase of the detection value $V_{max}$ of the reference coil and the detection value V(i) of the sensing coil 32(i) is larger than $|\pi/2|$, the polarity determination unit 463 determines that the polarity of the sensing coil 32(*i*) is opposite to the polarity of the reference coil (step S194).

For example, if the polarity of the sensing coil 32(1) set as the reference coil is set to be positive, in the case of FIG. 4, a line perpendicular to the vector indicating the detection value $V_{max}$ is defined as a boundary B, and the polarity of the sensing coil 32(2) corresponding to the vector (detection value V(2)) of the side closer to the vector indicating the detection value $V_{max}$ with respect to the boundary B is determined to be positive like the reference coil. The polarities of the sensing coils 32(3) to 32(5) corresponding to the vectors (detection values V(3) to V(5)) far from the vector indicating the detection value $V_{max}$ with respect to the boundary B are determined to be negative opposite to the polarity of the reference coil. After that, the process returns to the main routine.

In step S20 subsequent to step S19, the polarity determination unit 463 updates the determination results of polarities for the sensing coils 32(*i*) stored in the storage unit 43 to the determination results of polarities in step S19.

In step S21, the position-direction calculation unit 464 calculates the position and direction of the capsule endoscope 10 based on the polarities of the sensing coils 32(*i*), the amplitude values $V_{abs(i)}$ of the voltages, and the positions on the base 31 and the direction of the opening.

In step S22, the calculation unit 46 outputs the calculation result (hereinafter, referred to as position-direction information) of the position and direction of the capsule endoscope 10. The control unit 49 stores the output position-direction information in the storage unit 43 in correspondence with the images based on the radio signal received by the reception unit 41 at the same timing as the detection of the AC magnetic field in step S1 and displays the position and direction of the capsule endoscope 10 in the output unit 47.

In step S23, the control unit 49 determines whether or not the position detection for the capsule endoscope 10 continues to be performed. The determination may be performed, for example, by determining whether or not a command for ending the examination is input from the operating unit 44 (if the command is input, the position detection does not continue to be performed), by determining whether or not the AC magnetic field can be detected from the marker coil (if the AC magnetic field cannot be detected, the position detection does not continue to be performed), or by determining the radio signal can be received from the capsule endoscope 10 (if the radio signal cannot be received, the position detection does not continue to be performed).

If the position detection continues to be performed (step S23: Yes), the operations of the position detection system 1 returns to step S11. In this case, the processes of steps S11 to S22 are repetitively performed in an output period of the A/D conversion trigger from the A/D controller 48.

On the other hand, if the position detection does not continue to be performed (step S23: No), the operations of the position detection system 1 are ended. If the AC magnetic field cannot be detected from the marker coil or if the radio signal cannot be received from the capsule endoscope 10, the determination may be performed again after waiting for a predetermined time, and the operations may be ended.

As described heretofore, in the first embodiment, the reference coil is set among the plurality of sensing coils 32(*i*), and the polarities of the sensing coils 32(*i*) are determined based on the polarity of the reference coil and the phase differences between the detection signal of the AC magnetic field detected by the reference coil and the detection signals of the AC magnetic field detected by the other sensing coil 32(*i*). That is, the determination of polarity can be performed without synchronizing the generation of the magnetic field by the marker coil 141 provided in the capsule endoscope 10 with the detection of the magnetic field by the sensing coils 32(*i*). Therefore, the polarities of the sensing coils 32(*i*) can be determined without complicating the configuration of the capsule endoscope 10, and the position and direction of the capsule endoscope 10 can be accurately detected by using the polarities.

Second Embodiment

Next, a second embodiment of the present invention will be described.

Figure 6:
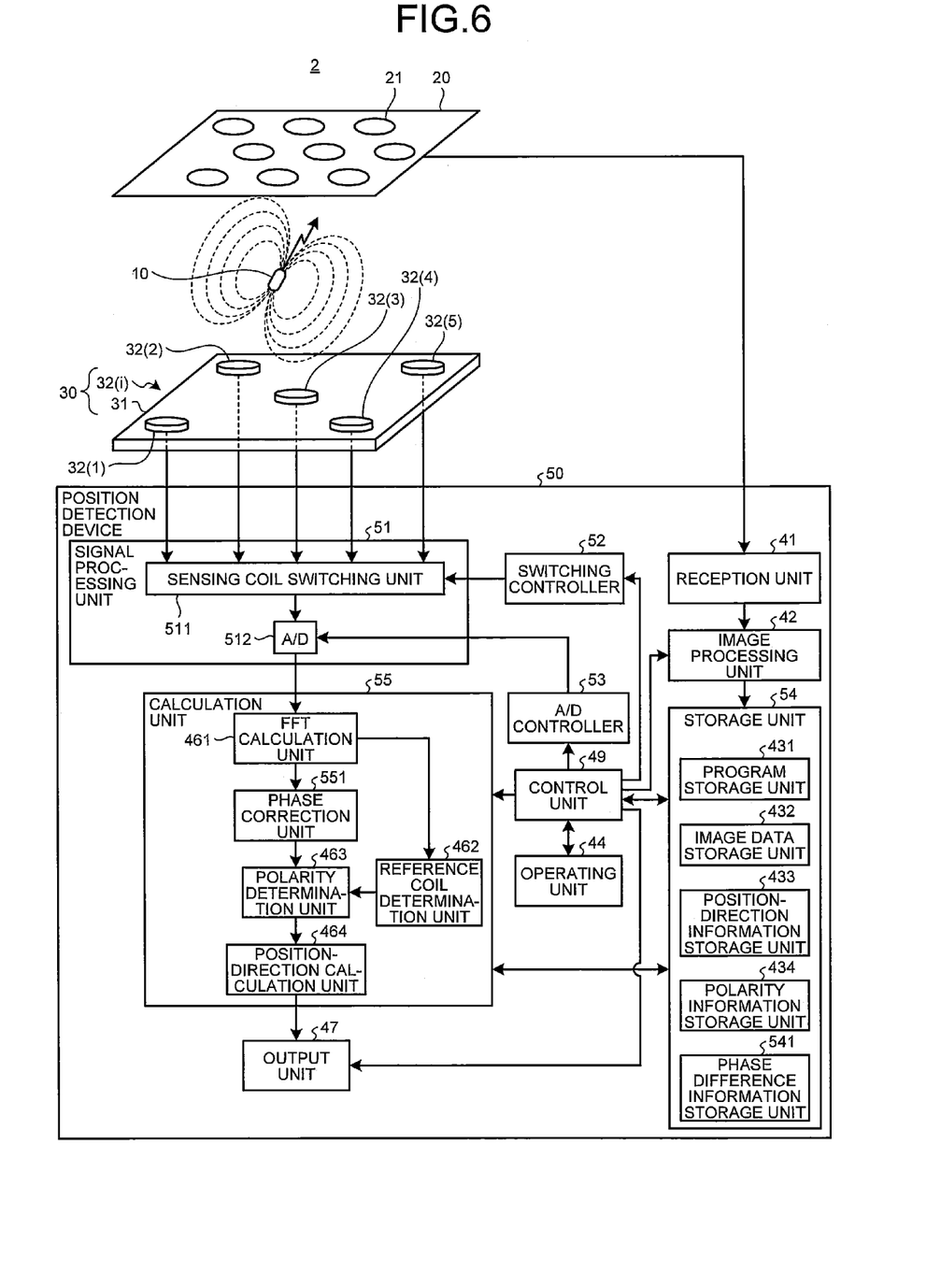
FIG. 6 is a schematic diagram illustrating a configuration example of a position detection system according to a second embodiment of the present invention.

FIG. 6 is a schematic diagram illustrating a configuration example of a position detection system according to the second embodiment of the present invention. As illustrated in FIG. 6, a position detection system 2 according to the second embodiment includes a position detection device 50 instead of the position detection device 40 illustrated in FIG. 1. Configurations and operations of the components of the position detection system 2 are the same as those of the first embodiment except for the position detection device 50.

The position detection device 50 includes a reception unit 41, an image processing unit 42, an operating unit 44, an output unit 47, a control unit 49, a signal processing unit 51, a switching controller 52, an A/D controller 53, a storage unit 54, and a calculation unit 55. Among them, the operations of the reception unit 41, the image processing unit 42, the operating unit 44, the output unit 47, and the control unit 49 are the same as those of the first embodiment.

The signal processing unit 51 includes a sensing coil switching unit 511 and an A/D converter (A/D) 512. Among the plurality of sensing coils 32(*i*), the sensing coil switching unit 511 switches one or a plurality of sensing coils 32(*i*) to be connected to the A/D converter 512 in a time division manner.

The switching controller 52 outputs a switching control signal to the sensing coil switching unit 511 so that the sensing coil switching unit switches the sensing coils 32(*i*) in a predetermined order at a predetermined timing.

The A/D controller 53 outputs a control signal (A/D conversion trigger) for operating the A/D converter 512 in a predetermined period.

The A/D converter 512 receives the detection signal from the connected sensing coil 32(*i*) at the timing when the A/D conversion trigger is output and performs the A/D conversion process.

Figure 7:
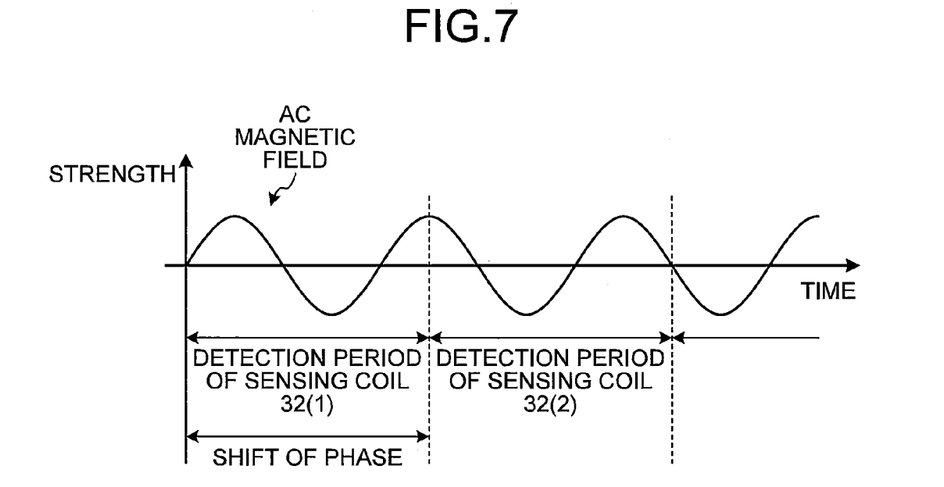
FIG. 7 is a schematic diagram illustrating phase shift occurring between detection signals when the detection signals are acquired from sensing coils in a time division manner.

In contrast with the storage unit 43 illustrated in FIG. 1, the storage unit 54 further includes a phase difference information storage unit 541. Here, if the A/D converter 512 receives the detection signals from the plurality of sensing coils 32(*i*) in the time division manner, as illustrated in FIG. 7, the shifts of the phases occur due to a difference in detection timing among the detection signals. The phase shift is a known value calculated from switching order and switching interval of the sensing coil 32(*i*) and a frequency of the AC magnetic field. The phase difference information storage unit 541 stores the shifts of the phases of the sensing coils 32(*i*) as phase difference information.

In contrast with the calculation unit 46 illustrated in FIG. 1, the calculation unit 55 further includes a phase correction unit 551. The phase correction unit 551 acquires the phase difference information from the phase difference information storage unit 541 and corrects the phases of the detection value V(i) of the sensing coils 32(*i*) calculated by the FFT calculation unit 461 by using the phase difference information.

Next, the operations of the position detection system 2 will be described. The overall operations of the position detection system 2 are the same as those illustrated in FIG. 3, but the operations are different from those of the first embodiment in that, in step S13, the detection signal is acquired from the plurality of sensing coils 32(i) in the time division manner, and the details of the polarity determination process for the sensing coils 32(i) in step S19 are different from those of the first embodiment.

Figure 8:
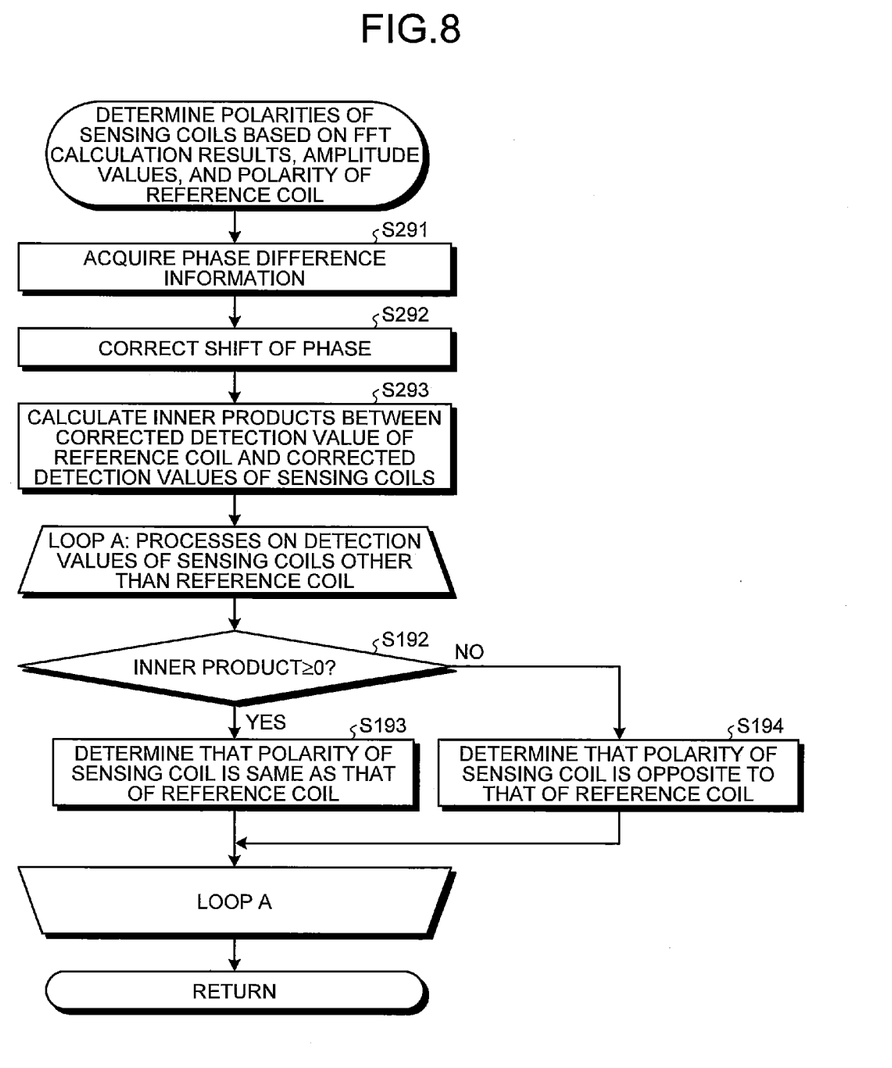
FIG. 8 is a flowchart illustrating a polarity determination process of the sensing coils in the second embodiment.

FIG. 8 is a flowchart illustrating the polarity determination process for the sensing coils 32(i) in the second embodiment. In step S291 illustrated in FIG. 8, the phase correction unit 551 acquires the phase difference information $\Delta\theta_i$ of the sensing coils 32(i) stored in the phase difference information storage unit 541.

Subsequently, in step S292, the phase correction unit 551 receives the detection values V(i) of the sensing coils from the FFT calculation unit 461 and corrects the shifts of the phases. The real part $x_{corr(i)}$ and the imaginary part $y_{corr(i)}$ of the corrected detection value V(i)' are given by the following equation (3) representing rotation transformation of a vector.

$$V(i)' = \begin{pmatrix} x_{corr(i)} \\ y_{corr(i)} \end{pmatrix} = \begin{pmatrix} \cos\Delta\theta_i & -\sin\Delta\theta_i \\ \sin\Delta\theta_i & \cos\Delta\theta_i \end{pmatrix} \begin{pmatrix} x_{meas(i)} \\ y_{meas(i)} \end{pmatrix} \quad (3)$$

Subsequently, in step S293, the polarity determination unit 463 calculates inner products $V_{max}' \cdot V(i)'$ between a corrected detection value $V_{max}'$ of the sensing coil 32(i) set as a reference coil and corrected detection values V(i)' of the other sensing coils 32(i). The subsequent operations after step S192 are the same as those of the first embodiment.

As described heretofore, according to the second embodiment, since the AC magnetic field is detected by the plurality of sensing coils 32(i) in a time division manner and the calculation is sequentially performed by the FFT calculation unit 461, the load of the calculation process of the calculation unit 55 can be reduced. In addition, according to the second embodiment, at this time, since the polarities of the sensing coils 32(i) are determined after the correction of the shifts of the phases according to the time, the polarities can be more accurately determined.

In the second embodiment, the correction of the detection value V(i) for each of the sensing coils 32(i) is performed according to the switching order of the sensing coils 32(i), but the detection values V(i) of the plurality of sensing coils 32(i) may be collectively corrected. For example, if the sensing coils 32(i) arranged on the base 31 are divided into plural systems (for example, L and R channels of an A/D converter for audio) and the sensing coils 32(i) are alternately operated for each of the systems, the same phase difference information for each of the systems are calculated and stored in advance, and the detection values V(i) for each of the systems may be collectively corrected.

Third Embodiment

Next, a third embodiment of the present invention will be described.

Figure 9:
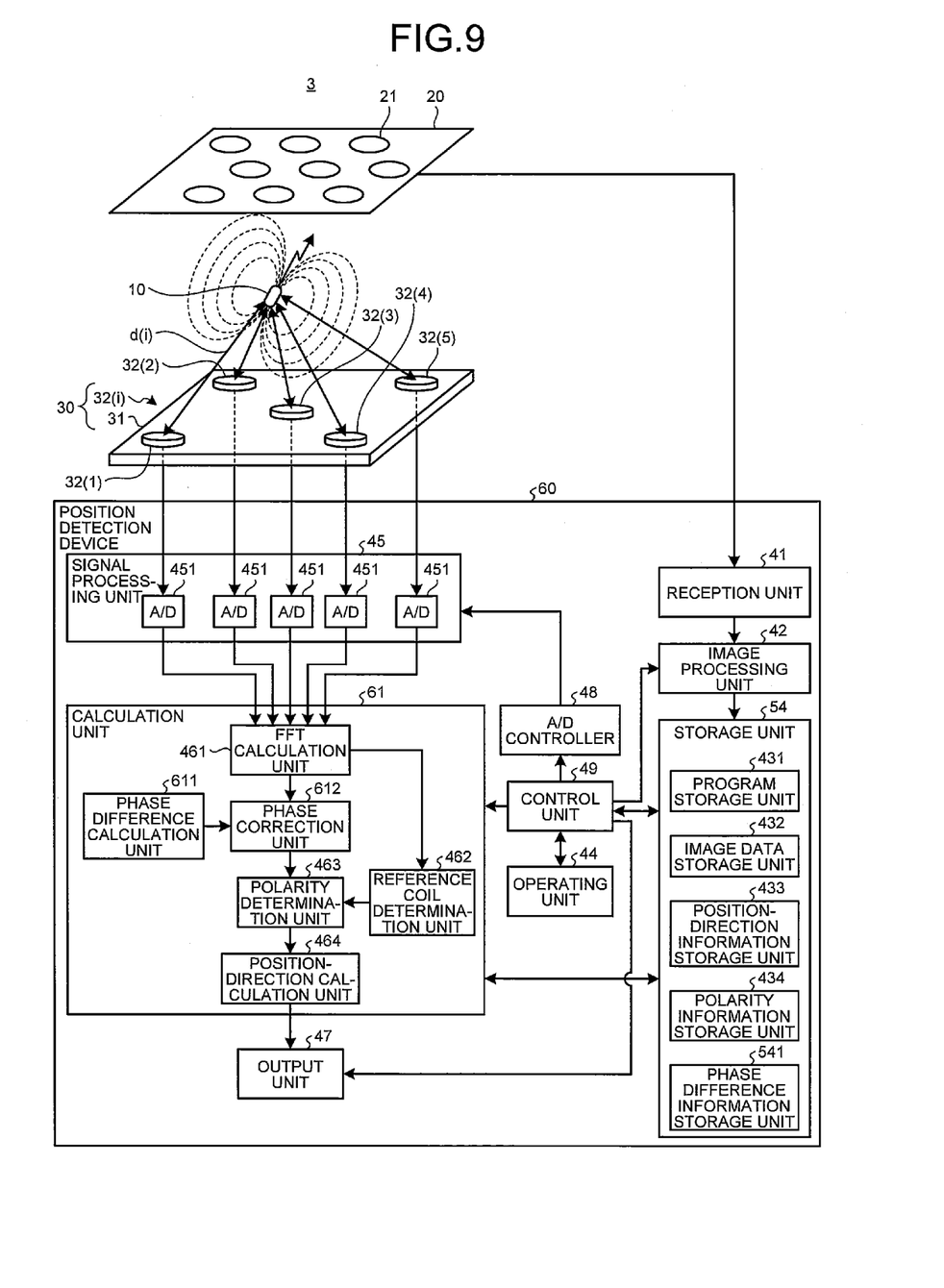
FIG. 9 is a schematic diagram illustrating a configuration example of a position detection system according to a third embodiment of the present invention.

FIG. 9 is a schematic diagram illustrating a configuration example of a position detection system according to the third embodiment of the present invention. As illustrated in FIG. 9, a position detection system 3 according to the third embodiment includes a position detection device 60 instead of the position detection device 40 illustrated in FIG. 1. Configurations and operations of the components of the position detection system 3 are the same as those of the first embodiment except for the position detection device 60.

The position detection device 60 includes a storage unit 54 and a calculation unit 61 instead of the storage unit 43 and the calculation unit 46 illustrated in FIG. 1. In contrast with the storage unit 43 illustrated in FIG. 1, the storage unit 54 further includes a phase difference information storage unit 541 which stores phase difference information indicating shifts of phases of detection signals detected by the sensing coils 32(i). In contrast with the calculation unit 46 illustrated in FIG. 1, the calculation unit 61 further includes a phase difference calculation unit 611 and a phase correction unit 612.

Figure 10:
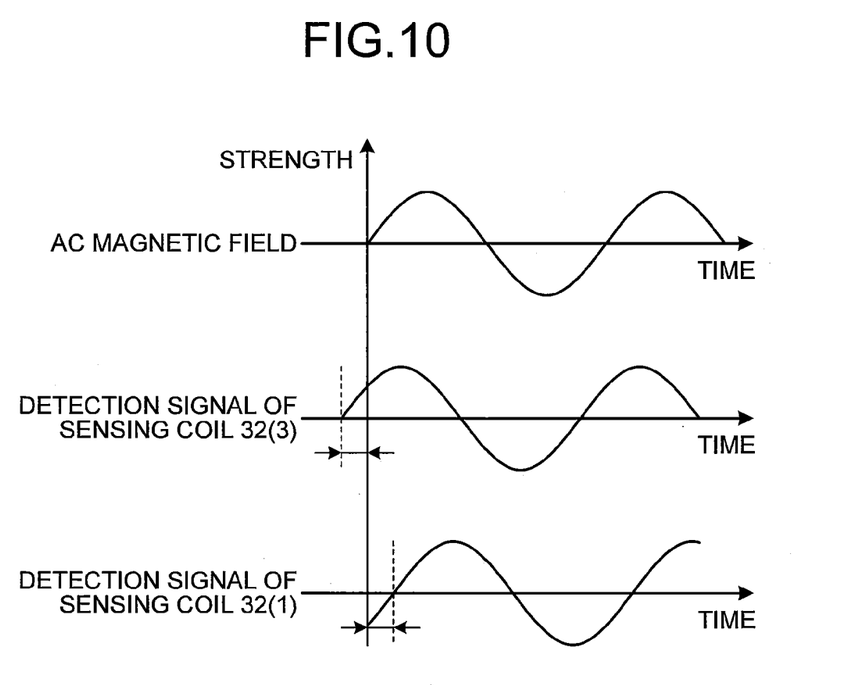
FIG. 10 is a schematic diagram illustrating a phase shift occurring between detection signals output from a plurality of sensing coils.

Herein, as illustrated in FIG. 10, the phase shift may occur among the detection signals of the AC magnetic field detected by the plurality of sensing coils 32(i) (for example, the sensing coils 32(1) and 32(3)) according to the distances d(i) of the sensing coils 32(i) from the capsule endoscope 10. The phase shift may also occur among the detection signals due to individual response characteristics (differences of individual sensing coils) of the sensing coils 32(i). Further, when the A/D conversion trigger is distributed from the A/D controller 48 to the A/D converters 451, slight difference in synchronization may occur, and the difference in synchronization may also lead to the phase shift among the detection signals.

The phase difference calculation unit 611 calculates the shifts of the phases among the detection signals occurring due to various reasons described above. The phase correction unit 612 corrects the phases of the detection value V(i) calculated by the FFT calculation unit 461 by using the phase difference information calculated by the phase difference calculation unit 611. The detailed operations of the phase correction unit 612 are the same as those of the phase correction unit 551 in the second embodiment (refer to FIG. 8).

Next, the operations of the position detection system 3 will be described. The overall operations of the position detection system 3 are the same as those illustrated in FIG. 3 and FIG. 5, but the operations are different from those of the first embodiment in that, in step S19, the polarity determination unit 463 uses the detection value V(i) obtained by the phase correction unit 612 correcting the calculation result of the FFT calculation unit 461.

Figure 11:
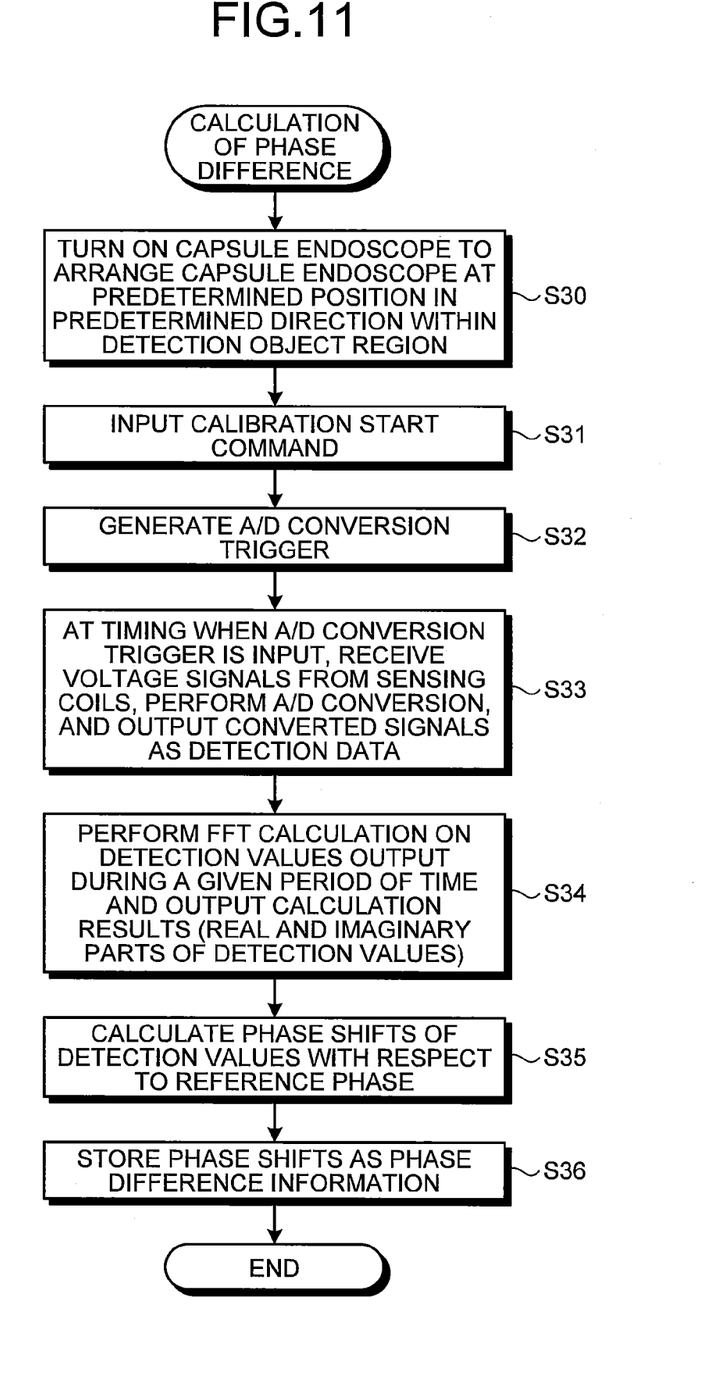
FIG. 11 is a flowchart illustrating a phase difference calculation method.

Next, the phase difference calculation method executed by the phase difference calculation unit 611 will be described. FIG. 11 is a flowchart illustrating the phase difference calculation method. First, in step S30, a user turns on the capsule endoscope 10 to generate an AC magnetic field, so that the capsule endoscope is arranged at a predetermined position in a predetermined direction within a detection object region of the magnetic field detector 30. At this time, the position of the capsule endoscope 10 is set to a position and direction in a case where the polarity information of each sensing coil 32(i) is known when the capsule endoscope 10 is arranged at the position. More specifically, the position and direction of a case where all the polarities of the sensing coils 32(i) are positive are acquired in advance, and the capsule endoscope is arranged at the position in the direction.

Subsequently, in step S31, the user inputs a calibration start command by using the operating unit 44. Accordingly, the command is input from the operating unit 44 to the control unit 49, and thus, under the control of the control unit 49, a calibration operation starts.

In step S32, the A/D controller 48 generates A/D conversion trigger for operating the plurality of A/D converters 451 in synchronization with each other.

In step S33, each A/D converter 451 receives the voltage signal from the sensing coil 32(i) at a timing when the A/D conversion trigger is input, performs A/D conversion on the voltage signal, and outputs the signal as detection data of the magnetic field.

In step S34, the FFT calculation unit 461 performs FFT calculation on the detection value of the voltage which is output as the detection data of the magnetic field from each A/D converter 451 during a given period of time and outputs the calculation result (real part and imaginary part of the detection value $V_{cal}(i)$) to the phase difference calculation unit 611.

In step S35, the phase difference calculation unit 611 calculates a phase shift of each detection value $V_{cal}(i)$ with respect to a predetermined reference phase. As a reference phase, a phase of a detection value $V_{cal}(i)$ of a sensing coil which is appropriately selected as a reference is used, such as a sensing coil having the lowest identification number (in FIG. 1, sensing coil 32(1)) or a sensing coil which is nearest from the capsule endoscope 10 (in FIG. 1, sensing coil 32(3)). At this time, if the polarity of the reference sensing coil 32(i) is positive, the phase of the detection value $V_{cal}(i)$ of the reference sensing coil 32(i) is set to 0, and the shifts of the phases of the detection values $V_{cal}(i)$ of the other sensing coils 32(i) are calculated. On the other hand, if the polarity of the reference sensing coil 32(i) is negative, the phase of the detection value $V_{cal}(i)$ of the reference sensing coil 32(i) is set to π, the shifts of the phases of the detection values $V_{cal}(i)$ of the other sensing coils 32(i) are calculated.

In step S36, the phase difference information storage unit 541 stores the phase shifts of the detection values V(i) calculated by the phase difference calculation unit 611 as phase difference information $\Delta\theta_i$ of the sensing coil 32(i).

As described heretofore, according to the third embodiment, since the phase shift of the detection value V(i) occurring due to the arrangement of the sensing coils 32(i), the differences of individual sensing coils, or the slight irregularity of the synchronization at the time of distributing the A/D conversion trigger is corrected, it is possible to more accurately determine the polarities of the sensing coils 32(i). Therefore, it is possible to further improve the accuracy of detection of the position and direction of the capsule endoscope 10.

According to some embodiments, since polarities of sensing coils are determined based on a detection signal output from a reference coil and detection signals output from the sensing coils, synchronization with a magnetic field generated by a marker coil is not necessary. It is therefore possible to determine the polarities of the sensing coils without complicating a configuration of a capsule medical device.

The first to third embodiments described heretofore are examples for embodying the present invention, but the present invention is not limited thereto. In the present invention, by appropriately combining the plurality of components disclosed in the first to third embodiments, various inventions can be contrived. It is obvious from the above disclosure that various modifications are available according to specifications or the like and various embodiments are available within the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position detection system for detecting a position of a capsule medical device, the capsule medical device having: a coil constituting a part of a resonance circuit to generate an AC magnetic field by flowing of current; a power source for supplying power to the coil; and a capsule casing, the coil and the power source being provided inside the casing, the position detection system comprising:
   a plurality of sensing coils configured to detect the AC magnetic field generated by the coil and to output detection signals; and
   a processor comprising hardware, the processor being configured to:
      calculate the position of the capsule medical device based on the plurality of detection signals output from the plurality of sensing coils,
      determine a first sensing coil having a maximum amplitude value of the AC magnetic field as a reference coil among the plurality of sensing coils based on amplitude values of the AC magnetic field detected by the plurality of sensing coils, the amplitude values being calculated based on the plurality of detection signals; and
      determine a polarity of each of the sensing coils based on a first detection signal output from the reference coil and a second detection signal output from a second sensing coil other than the reference coil among the plurality of sensing coils.

2. The position detection system according to claim 1, wherein the processor is further configured to determine the polarity of each of the sensing coils based on a comparison result between a phase of the first detection signal and a phase of the second detection signal.

3. The position detection system according to claim 2, wherein
   if a phase difference between the first detection signal and the second detection signal is equal to or smaller than $|\pi/2|$, the processor is further configured to determine that the polarity of the second sensing coil is equal to the polarity of the reference coil, and
   if a phase difference between the first detection signal and the second detection signal is larger than $|\pi/2|$, the processor is further configured to determine that the polarity of the second sensing coil is opposite to the polarity of the reference coil.

4. The position detection system according to claim 3, wherein
   the processor is further configured to:
      calculate the position of the capsule medical device at predetermined time intervals, and
      set the polarity of the first sensing coil determined as the reference coil to be the same polarity as a determination result for the first sensing coil obtained by previous determination of the polarity.

5. The position detection system according to claim 4, wherein if the determination result for the first sensing coil is not obtained by the previous determination of the polarity, the processor is further configured to set the polarity of the first sensing coil determined as the reference coil to be positive.

6. The position detection system according to claim 1, wherein the processor is further configured to correct a phase difference between the first detection signal and the second detection signal, the phase difference occurring due to a difference between timing of detecting operation for the AC magnetic field by the reference coil and timing of detecting operation for the AC magnetic field by each of the sensing coils.

7. The position detection system according to claim 6, wherein the processor is further configured to correct the phase difference based on a frequency of the AC magnetic field and an interval between the timing of detecting operation for the AC magnetic field by the reference coil and the timing of detecting operation for the AC magnetic field by each of the sensing coils.

8. The position detection system according to claim 6, wherein the processor is further configured to correct the phase difference based on a detection value of the AC magnetic field detected by each of the sensing coils when the capsule medical device is arranged at a position where the polarity of each of the sensing coils is known.

9. The position detection system according to claim 6, further comprising a switch configured to switch between the plurality of sensing coils to detect the AC magnetic field, wherein the processor is further configured to correct the phase difference according to a switching order of the plurality of sensing coils by the switch.

* * * * *